United States Patent [19]

Kappock et al.

[11] Patent Number: 5,518,774
[45] Date of Patent: May 21, 1996

[54] IN-CAN AND DRY COATING ANTIMICROBIAL

[75] Inventors: Paul S. Kappock, E. Hampton; Craig Waldron, Waterbury, both of Conn.

[73] Assignee: Olin Corporation, Cheshire, Conn.

[21] Appl. No.: 494,468

[22] Filed: Jun. 26, 1995

[51] Int. Cl.⁶ .............................. B05D 3/00; C09D 5/14; A01N 43/24

[52] U.S. Cl. .................. 427/384; 106/18.33; 106/18.36; 427/385.5; 514/183; 514/184; 514/191; 514/222.2; 514/494; 514/499; 523/122

[58] Field of Search ............................. 106/18.33, 18.36; 523/122; 427/372.2, 384, 385.5; 514/222.2, 183, 184, 191, 494, 499

[56] References Cited

U.S. PATENT DOCUMENTS

| | | | |
|---|---|---|---|
| 4,581,351 | 4/1986 | Berke et al. | 514/188 |
| 4,596,864 | 6/1986 | Trotz et al. | 526/265 |
| 5,057,153 | 10/1991 | Ruggiero | 106/18.33 |
| 5,098,473 | 3/1992 | Hani et al. | 106/18.33 |
| 5,185,033 | 2/1993 | Hani et al. | 106/18.33 |
| 5,246,489 | 9/1993 | Farmer, Jr. et al. | 106/18.33 |
| 5,252,123 | 10/1993 | Hani et al. | 106/18.33 |
| 5,342,437 | 8/1994 | Gavin et al. | 106/18.33 |

*Primary Examiner*—Anthony Green
*Attorney, Agent, or Firm*—Dale L. Carlson

[57] ABSTRACT

Disclosed are pyrithione-containing coating compositions exhibiting a combination of in-can preservation against microbial attack plus antimicrobial efficacy of the dry film resulting from the use of the coating composition on a substrate. Also disclosed is a process for imparting in-can and dry film antimicrobial efficacy to an aqueous coating composition.

8 Claims, No Drawings

IN-CAN AND DRY COATING ANTIMICROBIAL

FIELD OF THE INVENTION

This invention relates generally to coating compositions and, more specifically, to pyrithione-containing coating compositions exhibiting a combination of in-can preservation against microbial attack plus antimicrobial efficacy of the dry film resulting from the use of the coating composition on a substrate.

BACKGROUND OF THE INVENTION

Heretofore, coating compositions, such as latex paints containing pyrithione (typically in the form of zinc pyrithione) to provide antimicrobial protection of the paint in its "dry film" form after use, also generally require the presence of a supplemental antimicrobial additive, such as a hydrazine derivative, to provide "in-can" preservation of the paint against microbial (notably bacterial) attack during in-can storage of the paint prior to use. Unfortunately, these hydrazine derivative in-can preservatives are formaldehyde releasers, which poses a threat from an environmental, health and toxicity standpoint. New solutions to this problem must be found, particularly in view of the stringent air-quality standards required by the Clean Air Act of 1990.

Accordingly, there has been a recent push in the industry to satisfy a long-felt need for antimicrobial additives that provide a combination of effective in-can preservation and antimicrobial protection of the dry film coating without release of formaldehyde. The present invention provides one answer to this long-felt need.

SUMMARY OF THE INVENTION

In one aspect, the present invention relates to an aqueous coating composition comprising:
  (a) water,
  (b) a base medium (such as a polymer latex),
  (c) a zinc compound selected from the group consisting of zinc oxides, zinc hydroxide, zinc salts, and combinations thereof, and
  (d) a pyrithione salt (preferably sodium pyrithione) other than zinc pyrithione, alone or in combination with zinc pyrithione, said zinc compound plus said pyrithione salt being present in said composition in a total amount sufficient to provide in-can and dry film antimicrobial efficacy to said composition.

In another aspect, the present invention relates to a method for imparting a combination of in-can preservation against microbial growth and dry film antimicrobial effectiveness to an aqueous coating composition which comprises the steps of:
  (a) contacting said composition with a pyrithione salt (preferably sodium pyrithione) other than zinc pyrithione, in an amount of said pyrithione salt sufficient to impart to said composition in-can preservation against microbial attack, and
  (b) contacting said composition with a zinc compound selected from the group consisting of zinc oxides, zinc hydroxide, zinc salts, and combinations thereof, and reacting at least a portion of said zinc compound with at least a portion of said sodium pyrithione, thereby converting sodium pyrithione to zinc pyrithione in an amount sufficient to impart said dry film antimicrobial effectiveness to said coating composition.

A process for imparting in-can and dry film antimicrobial efficacy to an aqueous coating composition which comprises the steps of:
  (a) incorporating into the coating composition an in-can antimicrobially effective amount of said soluble pyrithione salt having a solubility at 20 degrees Centigrade of at least 4,000 ppm in said coating composition,
  (b) incorporating a metal ion-containing compound (such as a metal salt) into said coating composition to cause at least a portion of said metal ion-containing compound to transchelate with at least a portion of said soluble pyrithione salt, thereby forming a metal pyrithione-containing coating composition, said metal pyrithione having a solubility in said coating composition of less than 100 ppm,
  (c) contacting said metal pyrithione-containing coating composition with a substrate in order to form a metal pyrithione-containing coating on said substrate, and
  (d) drying said metal pyrithione-containing coating on said substrate to form a dry film on said substrate, said dry film containing a leach-resistant, antimicrobially effective amount of said metal pyrithione.

These and other aspects will become apparent upon reading the following detailed description of the invention.

DETAILED DESCRIPTION OF THE INVENTION

It has now been surprisingly found in accordance with the present invention that the transchelation of a relatively soluble pyrithione salt (such as sodium pyrithione) with a metal ion-containing compounds to form a more insoluble pyrithione salt (such as zinc pyrithione) affords an excellent combination of "in-can" and "dry film" antimicrobial protection to an aqueous coating composition. Thus, for example, inclusion of sodium pyrithione in an aqueous coating composition (such as a latex paint) together with a zinc compound (such as zinc oxide) provides a sodium pyrithione-containing coating composition exhibiting excellent in-can preservation against microbial growth, notably from bacteria, during in-can storage of the coating composition. In addition, this composition provides excellent "dry film" antimicrobial efficacy after coating a substrate with the coating composition by virtue of the transchelation of at least a portion of the sodium ions and zinc ions in aqueous solution, thereby forming more insoluble, leaching-out-resistant zinc pyrithione.

Without wishing to be bound by any particular theory, it is believed that the combination of in-can preservation and dry film antimicrobial efficacy associated with the compositions of the present invention is attributable (in the case, for example, of a sodium pyrithione and zinc oxide-containing coating composition) to a relatively slow conversion of a relatively soluble pyrithione salt (such as sodium pyrithione) by transchelation to a relatively insoluble pyrithione salt (such as zinc pyrithione) during in-can storage of the coating composition in an aqueous medium. In this example, the pyrithione moiety is primarily responsible for antimicrobial efficacy, whereas the specific metal counterion selected for use with the pyrithione (e.g., sodium) determines the solubility of the pyrithione moiety in the coating composition, and therefore the amount of active biocide available to provide "in-can" antimicrobial protection. In turn, the specific metal (e.g., zinc) ion employed in the pyrithione salt during use of the coating influences the rate of depletion of the pyrithione moiety from the dry film into the outdoor environment. Thus, before conversion by ion exchange, the sodium pyrithione (by virtue of its relatively high solubility in the coating composition) provides in-can protection to the coating composition, whereas after conversion, the resulting zinc pyrithione (a relatively insoluble compound) provides dry film protection to the coating on a substrate since the zinc pyrithione (or other relatively insoluble pyrithione such as copper pyrithione or titanium pyrithione) does not leach out of the dry coating as rapidly as more water-soluble pyrithiones, thereby ensuring longlasting antimicrobial protection of the dry coating.

Preferred metal ion-containing compounds for use in transchelation with the pyrithione salt in the aqueous coating composition include zinc compounds, such as the zinc salt of an organic acid or inorganic acid, such as zinc borate or zinc chloride, zinc hydroxide or zinc oxide, or a mixture thereof, in an amount sufficient to provide a molar ratio of pyrithione salt to metal ion-containing compound of between about 1:10 and about 10:1. Other useful metals include copper, for example in the form of copper oxide or copper sulfate, and titanium, suitably employed as titanium dioxide, and the like. The amount of the metal ion-containing compound employed in the aqueous coating composition can vary over a wide range of, for example, between 0.001% or lower to 10% or greater, preferably between 0.005% and 1%, based upon the weight of the coating composition. If a zinc compound is employed as the metal ion-containing compound, it is preferred that the amount of the zinc compound be sufficient to enable complete conversion of the pyrithione salt by transchelation to zinc pyrithione during storage of the coating composition.

Pyrithione salts useful as starting materials in preparing the antimicrobially effective coating compositions of the present invention include sodium pyrithione, tertiary butyl amine pyrithione, aluminum pyrithione, calcium pyrithione, potassium pyrithione, magnesium pyrithione, barium pyrithione, and the like. Sodium pyrithione is a preferred pyrithione salt, and zinc oxide is a preferred metal ion-containing compound for use in transchelation in accordance with the present invention. The amount of sodium pyrithione employed is advantageously between 0.1% and 2% (more advantageously between 0.2% and 1%, most advantageously between 0.25% and 0.8%), and the amount of zinc oxide employed is advantageously between about 1% and 10%, by weight, based upon the weight of the coating composition. The total amount of sodium pyrithione plus zinc oxide is advantageously between about 1% and 20% based on the total weight of the coating composition.

The sodium pyrithione useful in the present invention is a well-known commercial product that is commonly made by reacting 2-chloropyridine-N-oxide with NaSH and NaOH, as illustrated by the disclosures of U.S. Pat. No. 3,159,640. The sodium pyrithione is employed in the coating composition of the present invention in an antimicrobially effective amount, that is an amount sufficient to provide the desired "in-can" and "dry film" antimicrobial protection. Although the amount of the pyrithione can vary over a wide range, depending upon the specific application envisioned, it is preferred that the pyrithione be present in the coating composition in an amount of between about 100 ppm and about 5,000 ppm, which corresponds to a weight percent of pyrithione of between about 0.01% and about 0.5% based upon the weight of the coating composition.

The aqueous coating compositions of the present invention are suitable for a variety of uses, such as, for example as soap, shampoo, skin care medicaments, paint, or incorporated into or onto plastic or a woven or non-woven fibers, when formulated to contain the requisite components in addition to the antimicrobial component.

The antimicrobial compositions of the present invention are particularly useful in the form of paints, including indoor and outdoor household paints, industrial and commercial paints, particularly latex paints. The antimicrobial component of the aqueous composition is also useful as an "in-can" preservative during storage and prior to use of the paint.

Typically a paint composition will contain, in addition to the antimicrobial component, a resin, a pigment, and various optional additives such as thickening agent(s), wetting agents and the like, as is well known in the art. The resin is preferably selected from the group consisting of vinyl, epoxy, acrylic, polyurethane and polyester resins, and combinations of thereof. The resin is preferably employed in an amount of between about 20% and about 80% based upon the weight of the paint or paint base.

In addition, the paint composition of the present invention optionally additionally contains optional additives which have a favorable influence on the viscosity, the wetting power and the dispersibility, as well as on the stability to freezing and electrolytes and on the foaming properties. The total amount of optional additives is preferably no greater than 20% by weight, more preferably between about 1% and about 5% by weight, based upon the total weight of the paint composition.

Illustrative, thickening agents include cellulose 30 derivatives, for example methyl, hydroxyethyl, hydroxypropyl and carboxymethyl cellulose, poly(vinyl alcohol), poly (vinylpyrolidone), poly(ethyleneglycol), salts of poly(acrylic acid) and salts of acrylic acid/acrylamide copolymers.

Suitable wetting and dispersing agents include sodium polyphosphate, salts of low molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer 1.2-diols for example glycol, propylene glycol (1.2) and butylene glycol 1.2) or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation (white point) of the paint composition may be reduced by adding solvents, such as glycol ethers, ester alcohols or alkylated aromatic hydrocarbons. As defoaming agents there are suitable for example poly(propylene glycol) and polysiloxanes. Optionally other biocides can additionally be incorporated into the paint formulations of the present invention.

The paint composition of the present invention may be used as a paint for natural or synthetic materials, for example wood, paper, metals, textiles and plastics. It is particularly suitable as an indoor or outdoor latex paint.

Another significant use for the aqueous composition of the present invention is as a latex tile adhesive typically containing, for example, in addition to the antimicrobial component, a latex emulsion, an optional rosin emulsion, an optional plasticizer, an optional antioxidant, and an optional pigment or filler (such as calcium carbonate). Yet another significant use for the aqueous composition of the present invention is as a latex caulk or sealant, typically containing, in addition to the antimicrobial component, an acrylic latex, a nonionic surfactant, a dispersant, an optional plasticizer, and an optional pigment or filler (such as calcium carbonate).

The aqueous antimicrobial compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The invention is further illustrated by the following Examples. Unless otherwise stated, the "parts" and "%" are "parts by weight" and "percent by weight", respectively While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

The following examples are intended to illustrate, but in no way limit the scope of, the present invention.

EXAMPLE 1

Procedure used to make Acrylic Latex Paint Preparation of the Latex Using a Mill Base, Pigment Grind and Let-Down:

All ingredients in a mill base were added using a disperser blade at 300 RPM (slow). The ingredients were added slowly and upon completion allowed to mix for 5 minutes. The pigment grind was next. The titanium dioxide (Rutile) and zinc oxide were added slowly. Once all the titanium dioxide and zinc oxide were added, the mixing speed was increased to approximately 1000 RPM and allowed to grind for 5 minutes. Next, the mixing speed RPMs was lowered to 300, and aluminum magnesium silicate was added slowly. Upon completion of this addition, the mixing speed was again increased RPM to 1000, accompanied by continuous scraping of the sides of the vessel throughout this process. The mixing speed was then increased to 5000 RPM, and grinding was carried out for 5 minutes. The mixing speed was then lowered to 500 RPM, and the attapulgite clay was added before again increasing the mixing speed RPMs to 5000. The resulting mixture was thus blended for between 10 to 15 minutes, and hegman readings of the mixture were taken periodically until a reading of between 4–6 is achieved. This step involved about 10 minutes of grinding. The let down step then began with the addition of water to aid in the cooling. The mixing speed was slowed down to 250–300 RPM, and latex was added slowly during this step. The mixture was checked to be sure the pigments were not settling out during this process, and this mixture was blended at 250–300 RPMs for 10 minutes. Next, Colloid 643 dispersant was added with a syringe, at a mixing speed of 250 to 300 RPM, and mixing was continued for 5 minutes. Next, Texanol® surfactant was added with a syringe, at a mixing speed of 250–300 RPM, an mixing of the resulting mixture was continued for 5 minutes. The final step involved adding hydroxyethyl cellulose and or water to achieve the appropriate viscosity. The desired viscosity range in this case is 95–105 KU. The pH of the final mixture was 8.5. Amounts of the various additives employed in preparing this mixture are given in the following table:

TABLE 1

| Paint Components | | Amount of Paint Component in Grams |
|---|---|---|
| Mill base: | | |
| water | | 240.0 |
| hydroxyethyl cellulose | | 6.0 |
| Tamol 850[1/] | | 14.2 |
| Ethylene Glycol | | 50.0 |
| Colloid 643[2/] | | 2.0 |
| Triton ® CF-10[3/] | | 5.0 |
| sodium pyrithione 40% active | | 8.0 |
| potassium tripotyphosphate | | 3.0 |
| Pigment grind: | | |
| titanium dioxide (Rutile) | | 424.0 |
| aluminum magnesium silicate | | 228.0 |
| attapulgite clay | | 3.0 |
| zinc oxide | | 50.0 |
| aluminum silicate | | 100.0 |
| propylene glycol | | 68.0 |
| Let Down: | | |
| water | | 84.0 |
| acrylic latex emulsion | 58.0% solids | 700.0 |
| Colloid 643 | | 6.0 |
| Texanol ® [4/] | | 1.6 |
| hydroxyethyl cellulose | 2.5% in water | 236.4 |
| Total Mass In Grams | | 2248.2 |

Physical Properties of the paint of Example I:
Viscosity = 95.0 K.U.
pH = 8.5
Density = 11.50 lb./gallon
[1/]An anionic dispersant, a product of Rohm and Haas Company
[2/]A defoamer, a product of Rhone-Poutenc Corp.
[3/]A nonionic surfactant, a product of Union Carbide Corp.
[4/]A coalescent, a product of Eastman Kodak Company The paint of Example I containing sodium pyrithione and zinc oxide was monitored with time using HPLC liquid chromatography methodology. The results of the conversion of sodium pyrithione to zinc pyrithione with time is recorded below.

TABLE 2

| | HPLC Conversion Data | |
|---|---|---|
| Days After Production | % Sodium Pyrithione | % Zinc Pyrithione |
| 1 | 85 | 15 |
| 30 | 75 | 25 |
| 90 | 70 | 30 |
| 150 | 62 | 38 |

EXAMPLE 2

Sodium pyrithione efficacy as an "In-Can" Preservative

An acrylic latex paint was tested for protection from a *Pseudomonas aeruginosa* challenge for six weeks by using 1800 ppm of sodium pyrithione with or without 12.5 to 25 lb. of added zinc oxide per 100 gal.

Procedure

The present inventors were unable to establish a growth of Pseudomonas in the sample of latex paint, according to ASTM D2574. Consequently, they adopted the "Modified Springle Method" (J. Coatings Technol. 63: 33–38. 1991) in which the paint is diluted with water in order to simulate the conditions in which bacterial adaptation may occur in a paint factory. According to this procedure, undiluted paint represents product in the can, a 1:2 dilution (i.e., the volume ratio of paint to water) simulates dilution by condensation, and a 1:10 dilution simulates rinse water. Each of the samples was challenged with approximately 1% of contaminated paint from a previous experiment and monitored for survival during the first week. The samples were re-challenged with 1% of a 10% paint-adapted culture after the first and third weeks and then monitored through the remaining three weeks of the test.

Results

With the exception of the first week, the challenge did not survive in either the undiluted or 1:2 samples. However, the challenge survived the full six weeks in the 1:10 sample controls, but not in any of the sodium pyrithione-containing samples. The added zinc oxide did not appear to affect the challenge results. In consideration of the dilution factors, this response indicates a high degree of in-can antimicrobial protection afforded the paints of the present invention.

| Survival of Challenge (10% Dilution of Paint) | | | | | | | |
| --- | --- | --- | --- | --- | --- | --- | --- |
| Sample | day 1 | week 1 | week 2 | week 3 | week 4 | week 5 | week 6 |
| Blank | + | + | + | + | + | + | + |
| Sample 1 | + | + | + | + | + | + | + |
| Sample 2 | − | − | − | − | − | − | − |
| Sample 3 | − | + | + | + | + | + | + |
| Sample 4 | − | − | − | − | − | − | − |

Key to Sample numbers:

Sample 1 contains 1.25 wt. % Zn Oxide; Sample 2, 1.25 wt. % of Zn Oxide+1800 ppm or Na pyrithione; Sample 3, 2.5 wt. % Zn Oxide; and Sample 4, 2.5 wt. % of Zn Oxide+1800 ppm of Na pyrithione.

In the table, "+" denotes "growth" and "−" denotes "no growth".

Exposure Testing South Florida:

Paints containing 3 lbs/100 gallon, 4 lbs/100 gallon, 6 lbs/100 gallon of sodium pyrithione, and 25 lbs/100 gallon of zinc oxide all received perfect ratings of 10 (no mildew growth) after 6 months of exposure to the elements in testing at 45° South and vertical North in Miami, Fla.

What is claimed is:

1. An aqueous coating composition comprising:
   (a) water,
   (b) a base medium,
   (c) a zinc compound selected from the group consisting of zinc oxides, zinc hydroxide, zinc salts, and combinations thereof, and
   (d) a pyrithione salt other than zinc pyrithione, alone or in combination with zinc pyrithione, wherein said pyrithione salt is selected from the group consisting of sodium pyrithione, tertiary butyl amine pyrithione, aluminum pyrithione, calcium pyrithione, potassium pyrithione, magnesium pyrithione, barium pyrithione, and combinations thereof,
   wherein said zinc compound is present in said composition in an amount of between 0.001% and 10% based upon the weight of the composition, and wherein said pyrithione salt is present in said composition in a molar ratio of said pyrithione salt to said zinc compound of between about 1:10 and about 10:1.

2. The coating composition of claim 1 wherein said base medium is a polymer latex.

3. A method for imparting antimicrobial effectiveness to an aqueous coating composition which comprises the steps of:
   (a) contacting said composition with sodium pyrithione, in an amount of said sodium pyrithione of between 0.1% and 2% by weight based upon the weight of the coating composition, and
   (b) contacting said composition with zinc oxide, in an amount of between 1% and 10% by weight, based upon the weight of the coating composition, and reacting at least a portion of said zinc oxide with at least a portion of said sodium pyrithione, thereby converting sodium pyrithione to zinc pyrithione.

4. A process for coating a substrate with a coating composition to provide a coating exhibiting antimicrobial effectiveness on the substrate which comprises the steps of:
   (a) incorporating into the coating composition between about 0.01% and about 0.5% by weight, based upon the weight of the coating composition, of a soluble pyrithione salt having a solubility at 20 degrees Centigrade of at least 4,000 ppm in said coating composition,
   (b) incorporating a metal ion-containing compound into said coating composition in an amount of between 0.001% and 10% by weight, based upon the weight of the coating composition, to cause at least a portion of said metal ion-containing compound to transchelate with at least a portion of said soluble pyrithione salt, thereby forming a metal pyrithione-containing coating composition, said metal pyrithione having a solubility in said coating composition of less than 100 ppm,
   (c) contacting a substrate with said metal pyrithione-containing coating composition in order to form a metal pyrithione-containing coating on said substrate, and
   (d) drying said metal pyrithione-containing coating on said substrate to form a dry film on said substrate, said dry film containing a leach-resistant, antimicrobially effective amount of said metal pyrithione.

5. The process of claim 4 wherein said metal ion-containing compound is selected from the group consisting of metal salts, metal oxides, metal hydroxides, and combinations thereof.

6. The process of claim 4 wherein said metal ion-containing compound comprises a metal ion selected from the group consisting of zinc, copper, titanium, and combinations thereof.

7. The process of claim 4 wherein said soluble pyrithione salt is selected from the group consisting of sodium pyrithione, tertiary butyl amine pyrithione, aluminum pyrithione, calcium pyrithione, potassium pyrithione, magnesium pyrithione, barium pyrithione, and combinations thereof.

8. The process of claim 4 wherein the molar ratio of said soluble pyrithione salt to said metal ion-containing compound is between about 1:10 and about 10:1.

* * * * *